United States Patent [19]

Bergstrom et al.

[11] Patent Number: 5,250,613
[45] Date of Patent: Oct. 5, 1993

[54] SOLID SURFACE COATED WITH A HYDROPHILIC OUTER LAYER WITH COVALENTLY BONDED BIOPOLYMERS, A METHOD OF MAKING SUCH A SURFACE, AND A CONJUGATE THEREFOR

[75] Inventors: Karin Bergstrom, Kungälv; Krister Holmberg, Molndal, both of Sweden

[73] Assignee: Berol Nobel AB, Stenungsund, Sweden

[21] Appl. No.: 759,020

[22] Filed: Sep. 13, 1991

[30] Foreign Application Priority Data

Oct. 22, 1990 [SE] Sweden .................... 9003363

[51] Int. Cl.$^5$ .............. C08G 69/10; C08H 1/00; C08L 1/00
[52] U.S. Cl. .................. 525/54.1; 525/54.11
[58] Field of Search ............ 525/54.1, 54.11

[56] References Cited

U.S. PATENT DOCUMENTS 4,565,740 1/1986 Gölander et al. .............. 428/409

OTHER PUBLICATIONS

Nikitin "the Chemistry of Cellulose and Wood" S. Monson, Jerusalem (1966), Ch. IV, pp. 62-71.

*Primary Examiner*—John Kight, III
*Assistant Examiner*—Jeffrey Culpeper Mullis

[57] ABSTRACT

A solid surface having anionic groups capable of reacting with imino groups is provided with a hydrophilic outer surface layer comprising a covalently bonded biopolymer by a method selected from the group consisting of:

a) reacting a water-soluble conjugate comprising nonionic hydrophilic polymer covalently bonded to a polyethylene imine and at least partly to a biopolymer with anionic groups on the surface;

b) reacting a polyethylene imine substituted by nonionic hydrophilic polymer with anionic groups on the surface, and reacting biopolymer with reactive groups of the nonionic hydrophilic polymer in the presence of a reaction medium having a dielectric constant less than 10% of the dielectric constant of pure water; and c) reacting a polyethylene imine substituted by an anionic hydrophilic polymer derived from a nonionic hydrophilic polymer having a cloud point which is at least 5° C. above the temperature at which the final product is to be used, and having biopolymer-reactive groups, and reacting biopolymer forming covalent bonds with reactive groups of the nonionic polymer in a water-base reaction medium at a temperature which is more than 5° C. below the cloud point of the nonionic hydrophilic polymer in the reaction medium.

The product comprises a biopolymer immobilized on a hydrophilic solid surface having a hydrophilic layer, coupled thereto via a polyethylene imine, and accordingly has low spontaneous adsorption of proteins and other biopolymers through electrostatic attraction and/or hydrophobic interaction.

10 Claims, No Drawings

SOLID SURFACE COATED WITH A HYDROPHILIC OUTER LAYER WITH COVALENTLY BONDED BIOPOLYMERS, A METHOD OF MAKING SUCH A SURFACE, AND A CONJUGATE THEREFOR

The immobilization of proteins and other biopolymers to solid surfaces is an established technique for a number of biochemical applications, such as solid phase diagnostics, analysis with biosensors, affinity chromatography, extra-corporeal therapy, and bio-organic synthesis. In all of these cases, the biopolymer is bonded to a solid surface, and its biological activity then utilized for a specific purpose, such as in solid phase diagnostics, extracorporeal therapy, biological synthesis, and treatment of implants.

In solid phase diagnostics, an antibody is frequently immobilized on a plastic surface, usually of polystyrene. When in contact with a body fluid, the immobilized antibody bonds any antigen that may be present. The antibody-antigen complex is then detected by means of a labelled antibody. The labelling may be in the form of a radioactive isotope, a fluorescent group, or an enzyme conjugate.

In extracorporeal therapy, a biologically-active substance is bonded to a chamber through which the patient's blood is conducted. A current example of extracorporeal therapy is hemoperfusion across an immobilized immunostimulating substance. Interferons and interleukins are examples of such substances. Examples of diseases that can be treated by this technique are cancer and AIDS.

In bio-organic synthesis, use is made of enzymes for producing organic compounds. An appropriate use for bio-organic synthesis is lipid transformations, i.e. transforming a lipid, usually a triglyceride, into another lipid. Most enzymes are expensive, and frequent reuse is necessary to ensure good process economy. Consequently, the use of immobilized enzymes is of interest in most large-scale enzymatic processes.

In the treatment of implants, a biopolymer is bonded to the surface which comes into contact with biological tissue. The biopolymer, for example collagen, promotes tissue growth and stimulates cell colonization on the implant, resulting in an increased biocompatibility. This technique can be utilized also for in vitro treatment of cell culture dishes to improve cell adhesion.

The immobilization of proteins on both organic and inorganic surfaces is today a well-established technique (see Chapter 4, *Principles of Immobilization of Enzymes, Handbook of Enzyme Biotechnology*, Second Edition, Ellis Horwood Limited, 1985), and it is possible to bond a large amount of protein to the surface while retaining adequate biological activity.

However, it has been found that most solid surfaces are so constituted that they adsorb proteins and other biopolymers spontaneously. Such adsorption from aqueous solution is promoted primarily by two types of physical forces, electrostatic attraction, and hydrophobic interaction. Most surfaces at normal pH are negatively charged, but usually they also contain hydrophobic domains. A protein usually has positive, negative and hydrophobic seats, which means that a protein is attracted to most surfaces, on the one hand by electrostatic attraction between positive seats and negatively charged groups in the surface, and, on the other hand, by hydrophobic interaction between hydrophobic domains of the protein and the surface. This is described in, for example, *Surface and Interfacial Aspects of Biomedical Polymers*, Ed. J. D. Andrade, Plenum Press (1985), Vol. 2, p. 81.

Such nonspecific adsorption by electrostatic attraction and hydrophobic interaction is an undesired phenomenon for the above-mentioned applications. In solid phase diagnostics, it results in an impaired sensitivity and a shorter life of the diagnostic kit. In both extracorporeal therapy and in bio-organic synthesis, spontaneous adsorption causes impaired activity and a shorter product life.

One way of drastically reducing the adsorption proteins and other biopolymers on solid surfaces is to provide the surfaces with a layer of an uncharged hydrophilic polymer. One example of a polymer that has been used for this purpose is polyethylene glycol (see C. G. Golander, *Preparation and Properties of Functionalized Polymer Surfaces*, Dissertation, Royal Institute of Technology, Stockholm (1986), but other substances, such as polysaccharides, for example dextran, cellulose ethers and starch; polyvinyl alcohol; and neutral silica sol have also been used for this purpose.

By coating the surface with a layer of uncharged hydrophilic polymer, such as polyethylene glycol side chains or "tails", both electrostatic attraction and hydrophobic interaction can be avoided.

One way of attaching polyethylene glycol tails to a solid polymer surface is first, to subject the surface to so-called acidic etching, then to adsorb a cationic polymer, such as polyethylene imine, to the surface, and finally, to react a reactive polyethylene glycol derivative with available amino groups in the polyethylene imine layer. This technique has been described in *Prog. Colloid Polym. Sci.*, 74 113–119 (1987). During the acidic etching (which is carried out with potassium permanganate in concentrated sulphuric acid), carboxylic acid and sulphonic acid groups as well as sulphuric acid esters are formed on the surface, forming a highly negatively charged polymer surface, to which the cationic polyethylene imine is bonded very strongly by electrostatic forces. Furthermore, it is likely that upon drying salt bonds between ammonium (or amino) groups in the polyethylene imine and carboxylate and sulphonate groups on the surface gradually are transformed into amide or imide bonds, which gives an even stronger bond of the polyethylene imide to the surface.

Even though hydrophilized surfaces made by this technique, described in the above paper, give an improved repellency of biopolymers, adsorption by electrostatic attraction and hydrophobic interaction is still much too high for a number of applications.

Hydrophilic surfaces of this type are of great interest to, inter alia, the above-mentioned applications of immobilized proteins. To covalently bond protein to such a surface, it is necessary to introduce into the hydrophilic layer reactive functional groups serving as anchoring points for the protein. However, it has proved extremely difficult to covalently bond protein to thoroughly hydrophilic surfaces, even if the surfaces contain a high concentration of reactive groups. The hydrophilic surface does not attract the protein. On the contrary, it acts as a repellent, because it is energetically unfavorable for a protein in aqueous solution to approach such a surface. As a result, the amount of immobilized protein usually will be low, regardless of whether it is an antibody for solid phase diagnostics, an immuno-stimulating substance for extracorporeal therapy, or an enzyme for bio-organic synthesis.

Thus, there is a need for improved methods of immobilizing biopolymers to hydrophilic surfaces, as well as a need for making the hydrophilic surface even more highly developed to give low spontaneous adsorption. A thoroughly developed hydrophilic surface, on the other hand, renders the introduction of desirable biopolymers more difficult.

According to the invention, it has now proved possible to improve the immobilization of desirable polymers, while simultaneously obtaining a thoroughly developed hydrophilic surface of low spontaneous adsorption.

According to the invention, a solid surface having anionic groups capable of reacting with amino groups is provided with a hydrophilic outer surface layer comprising a covalently bonded biopolymer by a method selected from the group consisting of:

a) reacting a water-soluble conjugate comprising nonionic hydrophilic polymer covalently bonded to a polyethylene imine and at least partly to a biopolymer with anionic groups on the surface;

b) reacting a polyethylene imine substituted by nonionic hydrophilic polymer with anionic groups on the surface, and reacting biopolymer with reactive groups of the nonionic hydrophilic polymer in the presence of a reaction medium having a dielectric constant less than 10% of the dielectric constant of pure water; and c) reacting a polyethylene imine substituted by an anionic hydrophilic polymer derived from a nonionic hydrophilic polymer having a cloud point which is at least 5° C. above the temperature at which the final product is to be used, and having biopolymer-reactive groups, and reacting biopolymer forming covalent bonds with reactive groups of the nonionic polymer in a water-base reaction medium at a temperature which is more than 5° C. below the cloud point of the nonionic hydrophilic polymer in the reaction medium.

The product of this method is a solid surface with a hydrophilic outer surface layer comprising covalently bonded biopolymer and with nonionic hydrophilic polymer bonded to a polyethylene imine, bonded to anionic groups in the solid surface via amino groups. The method makes it possible to readily introduce hydrophilic nonionic polymer chains in such an amount that they constitute at least 50% by weight of the polyethylene imine, so that low spontaneous adsorption on the surface is ensured.

By first forming the water-soluble conjugate of the polyethylene imine derivative with hydrophilic nonionic polymer, and allowing the conjugate to adsorb on the negatively charged surface, a dense and thick hydrophilic surface layer is obtained.

According to the invention, the water-soluble conjugate can be synthesized by first reacting the polyethylene imine with a nonionic hydrophilic polymer having groups capable of reacting with the amino groups. Examples of such groups are oxirane rings, aldehyde groups, sulphonic acid esters, tresylate, mesylate, tosylate, cyanuric chloride, carbonyl imidazole, and active carboxylic acid esters. The ratio of reactive amino groups in the polyethylene imine to reactive groups in the nonionic polymer is adjusted such that the latter is bonded with a low number of bonds.

An alternative way of attaching hydrophilic nonionic polymer to the polyethylene imine is to react with the latter ethylene oxide, ethylene oxide and propylene oxide, butylene oxide and/or tetrahydrofuran, to the desired chain length. In the event that a copolymerization is carried out, the reactants can be distributed randomly or in blocks, or in a combination thereof. When alkoxylation is over, terminal hydroxyl groups are transformed into any of the above-mentioned reactive groups.

The biopolymer is then bonded in known manner, as described in the literature, such as the references cited earlier in this specification, to polyethylene imine derivatives by reaction between reactive groups on the hydrophilic nonionic polymer chains and functional groups on the biopolymer. The number of biopolymers bonded to each hydrophilic nonionic polymer chain may vary within wide limits, depending on the type of biopolymer and hydrophilic nonionic polymer, and on the desired degree of immobilization. Usually, at least 5% of the hydrophilic polymer chains have covalently bonded biopolymers. In the event that the nonionic hydrophilic polymer chains can have two or more groups reactive with the biopolymer, for example when they are derived from cellulose ethers, the number of covalently bonded biopolymers in each chain may be more than one. Many such coupling reactions for biopolymers, such as proteins, are described in the literature, for example in *Macromol. Chem. Phys.* 25 (1985) pp. 325–373. Bonding of the biopolymers is usually carried out in water as the reaction medium and is made easier by the fact that the polyethylene imine derivative is dissolved in the water and not applied to a solid surface. According to the invention, the immobilization can be further promoted if it is carried out in the reaction environment and under the conditions set forth in the processes b) and c) above, and which will be described in more detail hereinafter. When bonding is over, the remaining reactive groups are reacted with the hydrophilic nonionic polymer chains in some suitable manner, for example by reaction with 2-mercaptoethanol and 2-aminoethanol, resulting in a water-soluble conjugate suitable for application to a solid surface with anionic groups.

Bonding of the biopolymers may also be carried out by first coupling the hydrophilic nonionic polymer to the biopolymer and then reacting the resulting product in the above-mentioned manner with the polyethylene imine.

For bonding proteins and peptides, use is preferably made of amino, thiol or phenolic hydroxyl groups reacting by nucleophilic attack with the electrophilic reactive groups at the ends of the polyethylene glycol chains. Examples of such groups are epoxides, aldehydes, sulphonic acid esters, such as tresylate, mesylate and tosylate, cyanuric chlorides, carbonyl imidazoles and carboxylic acid esters. Glycoproteins and carbohydrates can be bonded inversely by attaching suitable groups, such as amino groups, to the ends of the polyethylene glycol chains, and causing them to react with aldehyde groups or carboxylic acid groups originally present or generated in the polysaccharide, for example by periodate oxidation. This technique is described in U.S. Pat. No. 4,217,338.

The resulting soluble conjugate is then adsorbed in a negatively charged solid surface. Examples of suitable surfaces are those which have a natural negative net charge, for example silica and glass, or those in which negative charges have been generated by chemical or physical means. Negative charges can be induced on organic polymer surfaces by, for example, acidic etching, i.e. treatment with potassium permanganate in concentrated sulphuric acid, or by plasma-or radiation-induced grafting of an anionic component, such as acrylic acid or methacrylic acid. Examples of organic polymers suitable for this purpose are polystyrene, polyvinyl chloride, polyethylene, polymethyl methacrylate, polycarbonate, polysulfone and cellulose acetate.

The method of immobilizing biopolymer to a surface by first bonding it in solution to a water-soluble polymer and then absorbing the soluble conjugate to the surface, has been described above. Bonding to bovine serum albumin is a technique occasionally used for proteins and peptides, and PCT/SE88/00243 describes the use of a hydrophobic water-soluble polymer, especially hydrophobic uncharged polysaccharide, for this purpose. The present invention, however, discloses a novel and improved principle. By bonding the biopolymer to the surface via a dense layer of hydrophilic nonionic polymer, there is obtained an uncharged hydrophilic background surface to which very little nonspecific adsorption occurs, simultaneously as the biopolymer which is anchored to spacer arms reaching far into the water phase, has high accessibility to, for example, antibody-antigen reactions.

The method of the present invention imparts to the layer of hydrophilic nonionic polymer a very high density, far higher than is obtained by direct bonding of hydrophilic nonionic polymer to a solid surface. The difficulty of obtaining a closely packed hydrophilic layer is that the individual hydrophilic nonionic polymers repel each other. The same repellency occurs of course also when polyethylene imine is reacted with hydrophilic nonionic polymer derivatives in solution. However, by first generating the graft polymer between hydrophilic nonionic polymers and polyethylene imine in solution, then bonding the biopolymer, and finally adsorbing this conjugate with the polyethylene imine on the solid surface, all hydrophilic nonionic polymer, and this applies both to those which have bonded the biopolymer and those which have a free end group, are forced over to the water side. In the two-dimensional perspective, the number of hydrophilic nonionic polymer facing the water side will then be twice as large as when the conjugate was dissolved in water.

According to the invention, it is also possible first to coat the solid surface containing anionic groups with the above-mentioned polyethylene imine derivative which consists of a polyethylene imine substituted by nonionic hydrophilic polymer, and then to bond the biopolymer via reactive groups in the nonionic hydrophilic polymer chains. By this technique, bonding takes place in the presence of a reaction medium having a dielectric constant of less than 10%, preferably less than 5%, of the dielectric constant of pure water. In the event that the nonionic hydrophilic polymer derives from a nonionic hydrophilic polymer having a cloud point which is at least 5° C. above the temperature at which the final product is to be used, the biopolymer can also be bonded in a water-based reaction medium at a temperature which is more than 5° C. below the cloud point of the nonionic hydrophilic polymer in the reaction medium. These methods of introducing biopolymers are described in U.S. Ser. No. 759,284 filed Sep. 13, 1991, and U.S. Ser. No. 759,018, filed Sep. 13, 1991, now U.S. Pat. No. 5,198,493, issued Mar. 30, 1993.

An especially preferred form of reaction medium having a low dielectric constant is a microemulsion. The amount of water in the microemulsion usually is from about 0.5 to about 25% by weight, preferably from 1 to 15% by weight.

The nonpolar reaction medium and the hydrophobic component in the microemulsion usually are an aliphatic hydrocarbon, such as hexane or nonane, or a broader distillation fraction, such as petroleum ether boiling over 60°-80° C. The hydrophobic component of the microemulsion usually constitutes from 63 to 98.5% by weight.

The surface-active component usually is a combination of a surface-active compound and a so-called auxiliary tenside. The surface-active substance may be anionic, cationic, amphoteric, or nonionic, while the auxiliary tenside usually is an alcohol or a low-molecular alkylene oxide adduct. Examples of conventional substances of this type are butanol, pentanol, hexanol, ethylene glycol monobutyl ether and diethylene glycol monobutyl ether. The amount of surface-active component usually constitutes from about 0.5 to about 20% by weight of the weight of the microemulsion.

It has been found especially advantageous to use a surface-active compound capable of forming microemulsions in the absence of an auxiliary tenside. Surface-active compounds having this ability are nonionic compounds which as a hydrophilic group have a polyalkylene glycol chain produced by polymerization of ethylene oxide or by combinations of ethylene oxide and propylene and/or butylene oxide, as well as ionic compounds having an ionic hydrophilic group in a non-terminal position on the hydrocarbon chain.

The preferred hydrophilic part of nonionic tensides is a polyethylene glycol chain which, in the most preferred case has an average length of between 3 and 8 ethylene oxide units. The hydrophobic part may derive from hydroxyl compounds or carboxyl compounds containing an alkyl chain from 8 to 20 carbon atoms, or of an alkyl aryl group from 9 to 24 carbon atoms. Examples of such compounds are ethylene oxide adducts of nonyl phenol, octyl phenol and fatty alcohols.

The preferred ionic tensides have anionic groups, such as sulphonate, sulphate, carboxylate, phosphate and phosphonate, sulphonate being especially preferred. If desired, these tensides may also contain alkylene oxide groups, such as ethylene oxide, as coupling agents between the anionic group and the hydrophobic group. The hydrophobic part may be an alkyl chain of from 10 to 22 carbon atoms, or of an alkyl aryl group of from 9 to 24 carbon atoms. A few ether, ester or amide groups may be in the hydrophobic part. Examples of suitable ionic compounds are di(2-ethylhexyl)sulphosuccinate and carboxymethylated nonyl phenol ethoxylates containing from 1 to 4 ethylene oxide groups.

It is also possible to utilize the unusual dependence on temperature exhibited by some nonionic water-soluble polymers and to immobilize the biopolymers in an aqueous environment. Thus, polyalkylene glycols and nonionic cellulose ethers exhibit a decreasing water solubility at elevated temperature. The mechanism behind this dependence on temperature has still not been fully explained, but it is assumed that the conformation of the ethylene oxide groups is changed in connection with an increase in temperature, making the ethylene oxide groups increasingly hydrophobic in character, and thus less soluble in water. At a given temperature, the water solubility of the polymer is so low that the solution separates into two phases. This temperature is usually termed the cloud point of the solution. Polyalkylene glycols and cellulose ethers can both be produced with defined cloud points, and especially useful are the polymers whose cloud points lie within the range from 10° to 100° C., preferably from 30° to 50° C. The nonionic hydrophilic polymer is hydrophilic at the temperature at which the protein-coated surface is used, and the cloud point is at least 5° C., preferably at least 10° C., above the temperature at which the protein-coated surface is used. A preferred protein immobilization temperature is from 3° C. below the flocculation temperature of the nonionic hydrophilic polymer in the reaction medium up to 50° C.

Examples of suitable polyalkylene glycols are those in which ethylene oxides and alkylene oxides having from 3 to 4 carbon atoms, or tetrahydrofuran, are randomly distributed or distributed in blocks. Especially suitable are polyalkylene glycols having a molecular weight of from 2,000 to 10,000 and containing one or more polyoxy propylene and polyoxyethylene blocks having a molecular weight of from 300 to 3,000. Other types of suitable polyalkylene glycols are adducts of ethylene oxide in combination with higher alkylene oxides, or tetrahydrofuran, with a dihydroxy or polyhydroxy compound, such as glycerol or pentaerythritol.

The cellulose ethers preferably have such a degree of polymerization that a 1% aqueous solution thereof has a viscosity of from 10 to 10,000 cP, preferably from 30 to 5,000 cP, measured according to Brookfield, LV, 12 rpm at 20° C. They may comprise hydrophobic hydrocarbon groups, such as methyl, ethyl, propyl, butyl, benzyl and higher hydrocarbon groups having from 8 to 24 carbon atoms, or polar hydroxyl groups, such as hydroxyethyl, hydroxypropyl and hydroxybutyl, or mixtures of hydrocarbon groups and polar groups, Examples of suitable cellulose ethers are methyl cellulose, ethyl cellulose, hydroxyethyl cellulose, hydroxypropyl cellulose, methyl hydroxyethyl cellulose, methyl hydroxypropyl cellulose, ethyl hydroxyethyl cellulose and benzyl ethyl hydroxyethyl cellulose. Alkyl hydroxyalkyl cellulose is the preferred cellulose ether.

The conjugate of polyethylene imine with hydrophilic polymer suitably comprises a polyethylene imine skeleton having a molecular weight of from 10,000 to 1,000,000, preferably from 50,000 to 500,000, containing secondary amino groups —$C_2H_4NH$—, tertiary amino groups —$C_2H_2N$—, and primary amino groups —$C_2H_4NH_2$—, in which preferably less than 20% of the reactive hydrogens of the primary and secondary amino groups are substituted by hydrophilic polymer side claims, and optionally, other substituents, such as alkyl groups, or hydroxyl group-containing groups utilized upon grafting of the hydrophilic polymer. The hydrophilic polymer suitably derives from nonionic alkylene oxide adducts, such as polyethylene glycol or randomly distributed or block-distributed polyalkylene glycols composed of ethylene oxide and alkylene oxides having from 3 to 4 carbon atoms, or tetrahydrofuran. Other types of alkylene oxide adducts are adducts of ethylene oxide, optionally in combination with higher alkylene oxides or tetrahydrofuran, with a dihydroxy or polyhydroxy compound, such as glycerol and pentaerythritol. Polysaccharides, such as dextran and starch; cellulose ethers, such as methyl cellulose, methyl hydroxypropyl cellulose, or ethyl hydroxyethyl cellulose; and polyvinyl alcohol are other suitable hydrophilic polymers. The hydrophilic polymers are water-soluble, and their molecular weight usually is from 400 to 200,000, preferably from 1,000 to 100,000.

The present invention is further illustrated by the following Examples, which represent preferred embodiments of the invention.

EXAMPLE 1

A square polyethylene plate 2 cm × 2 cm was washed in 70% ethanol for 3 minutes in an ultrasonic bath. The plate was air-dried, and then oxidized for 30 sec. in 2 g/l $KMnO_4/H_2SO_4$. The plate was rinsed with distilled water.

A solution containing 5% of human albumin and 10% of an epoxidized polyethylene glycol (PEG), obtained by adding 320 ethylene oxide units to di(trimethylol propane) was reacted for 15 hours at 30° C. at pH 7.0, after which the pH was adjusted to 9.5 with sodium hydroxide. Polyethylene imine (PEI) was added to a final concentration of 0 0.07%, and reacted therewith at 45° C. under agitation. After 2.5 hours, the polyethylene plate was placed in the solution, and the albumin-PEG-PEI complex was allowed to adsorb for 2 hours at 40° C.

The above was repeated, but as Control 2. Only the PEG-PEI adduct was synthesized as above, and the polyethylene plate was hydrophilized. Unreacted epoxides were reacted with mercaptoethanol. Also added to the reacted PEG-PEI adduct was albumin, and the copolymer with free albumin was allowed to adsorb to the polyethylene plate. The thickness of the PEG layer was determined by ellipsometry to 27 nm by first measuring the thickness of a layer of PEI alone and the thickness of the PEG-PEI layer, whereupon the former value was substracted from the latter.

The amount of bonded albumin was detected by ELISA technique with peroxidase-conjugated antibodies against albumin. The amount of adsorbed protein is proportional to the absorbency at 490 nm.

As Control 1, Control 2 was repeated, but without addition of the albumin.

The results were as follows.

TABLE I

| Example | OD 495 nm | PEG/PEI % by weight |
|---|---|---|
| Example 1 Immobilized albumin according to the invention | 1.266 | 78 |
| Control 1 without albumin | 0.054 | 78 |
| Control 2 with albumin | 0.178 | 78 |

The results show that the plate according to the invention has a high content of albumin, and that the hydrophilic layer has a low spontaneous adsorption of biopolymer.

EXAMPLE 2

A 96-well microtiter plate of polystyrene was grafted with crotonic acid and gamma-radiation.

A solution containing 0.07% polyethylene imine and 10% of a tresylated polyethylene glycol of molecular weight 7,000 was reacted for 2 hours at 37° C. and pH 9.0. Immunoglobulin G (IgG) was added up to a concentration of 1%, and allowed to react for a further 3 hours at 37° C. The solution was applied to the microtiter plate, and allowed to adsorb for 2 hours at 40° C.

As a Control, only the PEG-PEI adduct was synthesized as above, and the microtiter plate was hydrophilized. Unreacted tresylate groups were reacted with 1M sodium hydroxide.

The amount of bonded IgG was detected by ELISA technique with peroxidase-conjugated antibodies against IgG.

The following results were obtained.

TABLE II

| Example | OD 495 nm | PEG/PEI % by weight |
|---|---|---|
| Example 2 Immobilized IgG according to the invention | 0.983 | 80 |
| Control, without IgG | 0.026 | 80 |

The results show a high immobilization of IgG and a low spontaneous adsorption to the hydrophilic layer.

EXAMPLE 3

A PVC plate 2 cm×6 cm was activated in the same way as the polyethylene plate of Example 1.

A solution containing 2% fibrinogen and 5% of a block polymer of ethylene oxide and propylene oxide having a cloud point of 35° C. and having epoxide groups at both ends was allowed to react for 8 hours at 37° C. and at pH 7.0. Then, the pH was adjusted to 9.5 with sodium hydroxide, and polyethylene imine (PEI) was added to a final concentration of 0.03%. The reaction was allowed to proceed for 2.5 hours at 45° C. under agitation, after which the activated PVC plate was immersed in the solution, and the fibrinogen-block polymer-PEI complex was allowed to adsorb at 40° C. for 1 hour.

As a Control, use was made of a PVC plate hydrophilized with the block polymer-PEI adduct without protein, in which any remaining epoxide groups were reacted by treatment with 1M $HClO_4$ for 1 hour. The thickness of the block polymer layer was determined by ellipsometry to 30 nm by first measuring the thickness of the layer of PEI and the thickness of the block polymer-PEI layer, whereupon the former value was substracted from the latter.

The amount of bonded fibrinogen was detected by ELISA technique with peroxidase-conjugated antibodies against fibrinogen.

TABLE III

| Example | OD 495 nm | Block Polymer/PEI % by weight |
|---|---|---|
| Example 3 Immobilized fibrinogen according to the invention | 1.605 | 75 |
| Control, without fibrinogen | 0.070 | 75 |

The results show a high immobilization of fibrinogen and low spontaneous adsorption.

Having regard to the foregoing disclosure, the following is claimed as the inventive and patentable embodiments thereof:

1. A process for preparing an immobilized biopolymer immobilized on a solid surface and useful in biochemical application, comprising a reaction stage selected from the group consisting of
   a) reacting a water-soluble conjugate comprising nonionic hydrophilic polymer covalently bonded to a polyethylene imine and at least partly to a biopolymer, with anionic groups on the surface;
   b) reacting a polyethylene imine substituted by nonionic hydrophilic polymer with anionic groups on the surface, and reacting biopolymer is caused to react with reactive groups of the nonionic hydrophilic polymer in the presence of a reaction medium having a dielectric constant less than 10% of the dielectric constant of pure water; and
   c) reacting a polyethylene imine substituted by an anionic hydrophilic polymer derived from a nonionic hydrophilic polymer having a cloud point which is at least 5° C. above the temperature at which the immobilized biopolymer is to be used, and having biopolymer-reactive groups, and reacting biopolymer forming covalent bonds with reactive groups of the nonionic polymer in a water-base reaction medium at a temperature which is more than 5° C. below the cloud point of the nonionic hydrophilic polymer in the reaction medium; thereby forming a hydrophilic outer surface layer comprising a covalently bonded biopolymer and comprising nonionic polymer.

2. A process according to claim 1 in which the biopolymer is a protein or a peptide which is bonded, via an amino, thiol or phenolic hydroxyl group, to an epoxide group, an aldehyde group, a sulphonic acid ester group, a cyanuric chloride group, a carbonyl imidazole group or a carboxylic acid ester group in the hydrophilic nonionic polymer.

3. A process according to claim 1 in which the biopolymer comprises a carbohydrate group bonded, via an aldehyde group or carboxylic acid group to an $NH_2$ group in the hydrophilic nonionic polymer.

4. A process according to claim 1 in which the hydrophilic nonionic polymer comprises alkylene oxide adducts or cellulose ethers, the amount of the hydrophilic nonionic polymer being at least 50% by weight of the polyethylene imine.

5. A process according to claim 1 in which the solid surface is selected from polystyrene, polyvinyl chloride, polyethylene, polymethyl methacrylate, polycarbonate, polysulfone or cellulose acetate activated with carboxyl groups or aldehyde groups which are caused to react with amino groups of the water-soluble conjugate or with amino groups of the polyethylene imine derivative.

6. An immobilized biopolymer immobilized on a solid surface and useful in biochemical applications, the solid surface having a hydrophilic outer surface layer having covalently bonded biopolymer and nonionic polymer comprising nonionic polymer covalently bonded to a polyethylene imine which in turn is bonded to the solid surface via anionic groups of the surface reacted with imino groups thereof, the weight of the nonionic polymer being at least 50% by weight of the polyethylene imine.

7. An immobilized biopolymer according to claim 6 in which the biopolymer is a protein which is bonded, via an amino, thiol or phenolic hydroxyl group, to an epoxide group, an aldehyde group, a sulphonic acid ester group, a cyanuric chloride group, a carbonyl imidazole group, or a carboxylic acid ester group in the hydrophilic nonionic polymer.

8. An immobilized biopolymer according to claim 6 in which the biopolymer contains carbohydrate groups bonded, via an aldehyde group or carboxylic acid group, to an $NH_2$ group in the hydrophilic nonionic polymer.

9. An immobilized biopolymer according to claim 6 in which the hydrophilic nonionic polymer comprises chains of alkylene oxide adducts or cellulose ethers, the amount of the hydrophilic nonionic polymer chains being at least 50% by weight of the polyethylene imine.

10. An immobilized biopolymer according to claim 6 in which the solid surface is selected from polystyrene, polyvinyl chloride, polyethylene, polymethyl methacrylate, polycarbonate, polysulfone or cellulose acetate activated with carboxyl groups or aldehyde groups which are caused to react with amino groups of the water-soluble conjugate or with imino groups of the polyethylene imine.

* * * * *